United States Patent [19]

Meriläinen

[11] Patent Number: 4,763,664
[45] Date of Patent: Aug. 16, 1988

[54] GAS COLLECTOR UNIT FOR MEASURING THE METABOLIC VARIABLES OF SELF-RESPIRING PATIENTS

[75] Inventor: Pekka Meriläinen, Helsinki, Finland

[73] Assignee: Instrumentarium Corp., Finland

[21] Appl. No.: 25,381

[22] Filed: Mar. 13, 1987

[30] Foreign Application Priority Data

Mar. 26, 1986 [FI] Finland ................................ 861289

[51] Int. Cl.[4] .............................................. A61B 5/08
[52] U.S. Cl. .................................. 128/718; 128/201.23; 128/202.26; 128/719
[58] Field of Search ................... 128/718, 719, 201.23, 128/201.24, 205.25, 205.26

[56] References Cited

U.S. PATENT DOCUMENTS 2,262,522 11/1941 Yant et al. .................. 128/201.23 X
2,484,217 10/1949 Gardenier .......................... 128/719
2,916,033 12/1959 Coleman ............................ 128/718
3,395,701 8/1968 Bartlett, Jr. et al. ............... 128/719
4,407,280 10/1983 Trammell et al. ............. 128/205.26

Primary Examiner—Lloyd L. King
Attorney, Agent, or Firm—Andrus, Sceales, Starke & Sawall

[57] ABSTRACT

A gas collector unit to be fitted over the head of a patient for measuring oxygen consumption, carbon dioxide output and respiratory quotient, said unit comprising a clear, substantially half-ellipsoidal plastic canopy (1), a cylinder of plastic sheeting (8), which is airtightly seamed to its edges and whose mouth (10) can be airtightly sealed around the neck of a patient, as well as hose couplings (2) and (3) and flow diffusers (6) and (7) associated therewith. The free volume of a canopy with a patient's head therein is less than a third of the amount air flowing through the canopy per minute and that the free cross-sectional area of a canopy perpendicular to flow is dimensioned in a manner that the average speed of air flow over the face is higher than 4 cm/s and the $CO_2$-content of inhalation air is less than 0.2%.

5 Claims, 1 Drawing Sheet

GAS COLLECTOR UNIT FOR MEASURING THE METABOLIC VARIABLES OF SELF-RESPIRING PATIENTS

BACKGROUND OF THE INVENTION

Human metabolism can be monitored by means of so-called indirect calorimetry wherein, by measuring the contents and flow rate of respiratory gases, it is possible to determine oxygen consumption ($\dot{V}_{O2}$) and carbon dioxide output ($\dot{V}_{CO2}$) On the basis of these, it is further possible to calculate an estimate for daily energy consumption as well as respiratory quotient ($RQ = \dot{V}_{CO2}/\dot{V}_{O2}$) which indicates the type of nutrition burning in the body. When burning carbohydrates, the amount of carbon dioxide produced is equal to the amount of oxtgen consumed, whereby $RQ=1$ while on fat the corresponding ratio $RQ=0.7$.

Indirect calorimetry is applied especially in the intensive care wards of a hospital for the quantitative and qualitative estimation of the nutritiqn demand of intravenously fed critically ill patients. Quite a few of these patients are placed in a respirator, the collection of exhalation gas to be measured being simple. However, the measuring involves several technical difficulties that have impeded spreading of this method in routine clinical application. Lately, there has been a dramatically growing scientific and also practical clinical interest to apply indirect calorimetry also to patients that are severely ill but capable of breathing on their own. This includes e.g. patients who suffer from cnacer and various metabolic diseases.

One apparatus intended for measuring patients connected to a respirator has been disclosed in Finnish Patent application No. 844562. By virtue of a constant flow aspirator included therein, said apparatus can be readily modified for applying it also to the measurement of self-respiring patients, as long as the collection of respiratory gases can be performed without substantially disturbing the patient.

The collection of respiratory gases is generally effected by means of a tight mask covering the nose and mouth or by means of a tube placed in the mouth, in which case the nose is closed by a separate clamp. However, the use of these instruments has been found (1) to disturb a patient to such a degree that respiration changes decisively and a state of balance required for the reliable measurement of metabolic variables cannot be reached during the time a patient can usually tolerate said instruments on his or her face. Various solutions have been developed for this problem, wherein e.g. the head of a patient is placed in a closed or half-open box with a continuous airstream passed therethrough. A particularly known device is "a canopy" (2), developed by Prof. John M. Kinney at the Columbia University, New York, which is an acrylic-made, transparent, hinged, rectangular box associated with a separate element to be sealed around the neck of a patient. Typical of this solution is that the box has such a great volume and is of such a design that the exhalation gas is evenly distributed in the space prior to leaving it.

Thus, the patient is forced to re-inhale rather high carbon dioxide contents. If the air flow passed through the box is 50 l/min and the patient has $V_{CO2}=250$ ml/min, the $CO_2$-content will be 0.5%. Since the measurement of gas contents this low at a high accuracy is difficult, an attempt is made to keep the air flow as low as possible for reaching higher $CO_2$-contents to be measured.

According to Prof. Kinney, the accepted maximum content of $CO_2$ is 1%. Above this, the carbon dioxide begins to stimulate respiration and, in view of metabolic measurements, the results begin to vary. On the other hand, according the subjective experience encountered by patients, considerably lower $CO_2$-contents can bring about a constricting sensation and change respiration.

SUMMARY OF THE INVENTION

This invention introduces a lightweight and, if necessary, disposable gas collector unit, which covers the head of a patient and is dimensioned and designed in a manner that re-inhalation of carbon dioxide is little but, on the other hand, the amplitude of a gas signal required for good measuring accuracy remains high as a non-uniform signal will be measured instead of a uniform one.

DESCRIPTION OF THE DRAWINGS

A sketch of a unit, hereinafter called a canopy, is shown in FIG. 1.

The position of a patient's head in a canopy is shown in FIG 2.

DESCRIPTION OF THE ILLUSTRATED EMBODIMENT

Figure 1:
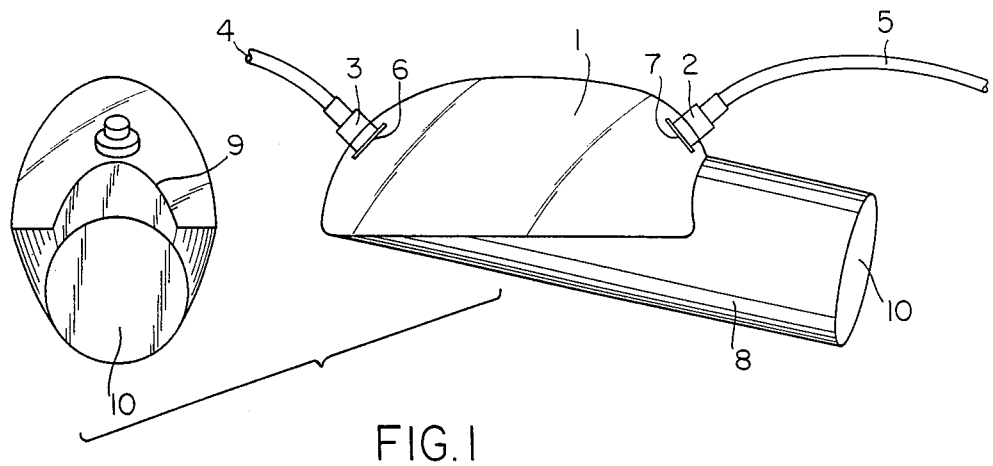

The canopy has a top section 1 which is moulded of bright, optically high-quality plastics and whose shape is close to a half-ellipsoid. Fitted in holes at the ends of this top section are hose couplings 2 and 3, to which are connected an air inlet hose 4 and an outlet hose 5. The hose couplings are provided with flat flow diffusers 6 and 7, the turbulences created thereby reducing the sensation of draught experienced by a patient on his or her face. To the lower edge of said top section is seamed in an airtight manner a plastic sheeting 8, extending as a closed cylinder past the end of the top section facing said outlet hose. The canopy is threaded as a single unit over the head of a patient, whereby the mouth of said cylindrical sheeting can be gently sealed around the neck of a patient. Optionally, it is possible to employ an open structure, the canopy being lowered directly over a patient and a plastic sheeting seamed to its edge is folded below a patient's head or a pillow and around the neck. During the measurement, a patient is normally in a lying position in the canopy. The edge of the top section of such canopy is designed to be semi-circular over an area 9 below the outlet hose coupling for fitting the neck of a patient therein.

Figure 2:
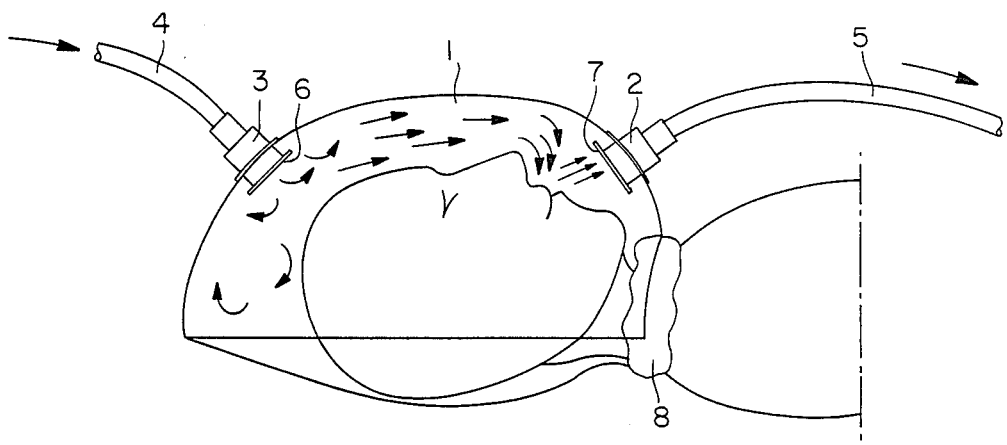

FIG. 2 illustrates the position of a patient's head in a canopy. The canopy is designed and dimensioned in a manner that the air flow rate over the nose and mouth of a patient remains sufficiently high. An accurate calculatory analysis is difficult as a result of varying head sizes and positions inside a canopy. Therefore, the dimensioning has been determined partly experimentally by measuring the $CO_2$-content of the inhalation air of a person inside a canopy by means of a $CO_2$-analyzer provided with a nose adapter. The objective has been to obtain a $CO_2$-content on a level of $0.1 \ldots 0.2\%$ $CO_2$.

The essential factors for making the $CO_2$-content low during the inhalation step are that the free cross-sectional area of a canopy perpendicular to the flow over a patient's face is sufficiently small, that the total volume of a canopy proportionated to the air flow is small, and that the direction of flow inside a canopy is such that exhalation from the nose is directed towards the air outlet. The free volume of a canopy dimensioned for adults, with the head inside, will be 15 ... 20 l and the cross-sectional area will be circa 200 cm², the air travelling at circa 4 cm/s at a flow rate of 50 l/min and the gas changing in a canopy circa 3 times a minute.

The tightness requirement for a canopy on patients breathing ambient air is not quite absolute since there is normally a little underpressure inside a canopy and the leaks are directed inwards without affecting the measuring result. However, the situation changes during a powerful, sigh-like exhalation when, if a momentary exhalation flow overcomes the aspirator flow, a flow at the inlet of a canopy will be reversed. This situation is taken care of by a spare volume in the inlet hose of a canopy but, if leaks occur elsewhere, some carbon dioxide might escape through those. If a gas whose oxygen content is higher than that of ambient air is aspirated into a canopy, the tightness requirement is definitely absolute. Although the clinical interest is mainly directed at measuring a patient who is at rest and in a lying position, the present canopy is designed so as to stay on the head also in an erect position. Hence, in principle, it can also be used for physiological stress test measurements, at least when using a bicycle ergometer. Of course, these measurements require the use of considerably stronger airstreams through a canopy than what is required for measurements in a state of rest.

I claim:

1. A gas collector unit to be fitted over the head of a patient for measuring oxygen consumption, carbon dioxide output and respiratory quotient, said unit comprising a clear, substantially half-ellipsoidal plastic canopy (1), a cylinder of plastic sheeting (8), which is seamed airtightly to its edges and whose mouth (10) can be sealed airtightly around the neck of a patient, as well as hose couplings (2) and (3) and flow diffusers (6) and (7) associated therewith, characterized in that the free volume of a canopy with a patient's head therein is less than a third of the amount of air flowing through the canopy per minute and that the free cross-sectional area of said canopy perpendicular to flow is dimensioned in a manner that the average speed of air flow over the face is higher than 4 cm/s and the $CO_2$-content of inhalation air is less than 0.2%.

2. A gas collector unit as set forth in claim 1, characterized in that the edges of plastic canopy (1) is provided with an open skirt of plastic sheeting seamed thereto.

3. An apparatus, comprising a gas collector unit as set forth in claim 1, a constant flow aspirator, $CO_2$- and $O_2$-sensors and calculator units, intended for measuring metabolic variables, characterized in that gas measurements are effected from gas signals, varying non-uniformly along with respiration and diluted by a constant flow.

4. The application of an apparatus as set forth in claim 1, for measuring the metabolic variables of a self-respiring patient.

5. The application of an apparatus as set forth in claim 1, for physiological stress test measurements.

* * * * *